(12) United States Patent
Connolly

(10) Patent No.: US 7,344,867 B2
(45) Date of Patent: Mar. 18, 2008

(54) SELECTION AND USE OF LACTIC ACID BACTERIA FOR REDUCING INFLAMMATION IN MAMMALS

(76) Inventor: Eamonn Connolly, BioGaia AB, Box 32, SE-443 21 Lerum (SE)

(*) Notice: Subject to any disclaimer, the term of this patent is extended or adjusted under 35 U.S.C. 154(b) by 0 days.

(21) Appl. No.: 11/107,438

(22) Filed: Apr. 15, 2005

(65) Prior Publication Data

US 2006/0233775 A1 Oct. 19, 2006

(51) Int. Cl.
*C12N 1/00* (2006.01)
*C12N 1/20* (2006.01)

(52) U.S. Cl. .................... 435/93.45; 435/853

(58) Field of Classification Search ............... None
See application file for complete search history.

(56) References Cited

U.S. PATENT DOCUMENTS

| | | | |
|---|---|---|---|
| 5,439,678 | A | 8/1995 | Dobrogosz et al. |
| 5,458,875 | A | 10/1995 | Casas-Perez et al. |
| 5,534,253 | A | 7/1996 | Casas et al. |
| 5,837,238 | A | 11/1998 | Casas et al. |
| 5,849,289 | A | 12/1998 | Dobrogosz et al. |
| 2002/0086981 | A1* | 7/2002 | Cirillo .................. 536/23.1 |
| 2003/0235559 | A1* | 12/2003 | Sobol et al. ............... 424/93.4 |
| 2004/0067573 | A1 | 4/2004 | Connolly et al. |
| 2004/0208863 | A1 | 10/2004 | Versalovic et al. |

* cited by examiner

*Primary Examiner*—David M Naff
*Assistant Examiner*—Deborah K. Ware
(74) *Attorney, Agent, or Firm*—Lynn E. Barber

(57) ABSTRACT

Strains of lactic acid bacteria selected for their capability of reducing inflammation, such as intestinal bowel disease, a method of selecting such strains, and products containing such strains.

2 Claims, 4 Drawing Sheets

|  | | No LPS Control | LPS Control |
|---|---|---|---|
| CD-R | Control - Rem | 0 | 246.5 |
| | MRS - Rem | 0 | 118.2 |
| | MM4-1 - Rem | 17.82 | 67.84 |

|  | | No LPS Control | LPS Control |
|---|---|---|---|
| CD-A | Control - Act | 0.93 | 290.73 |
| | MRS - Act | 2.62 | 186.49 |
| | MM4-1 - Act | 27.3 | 102.04 |

Detection limit for TNF-alpha ELISA : 15pg/ml to 1000 pg/ml

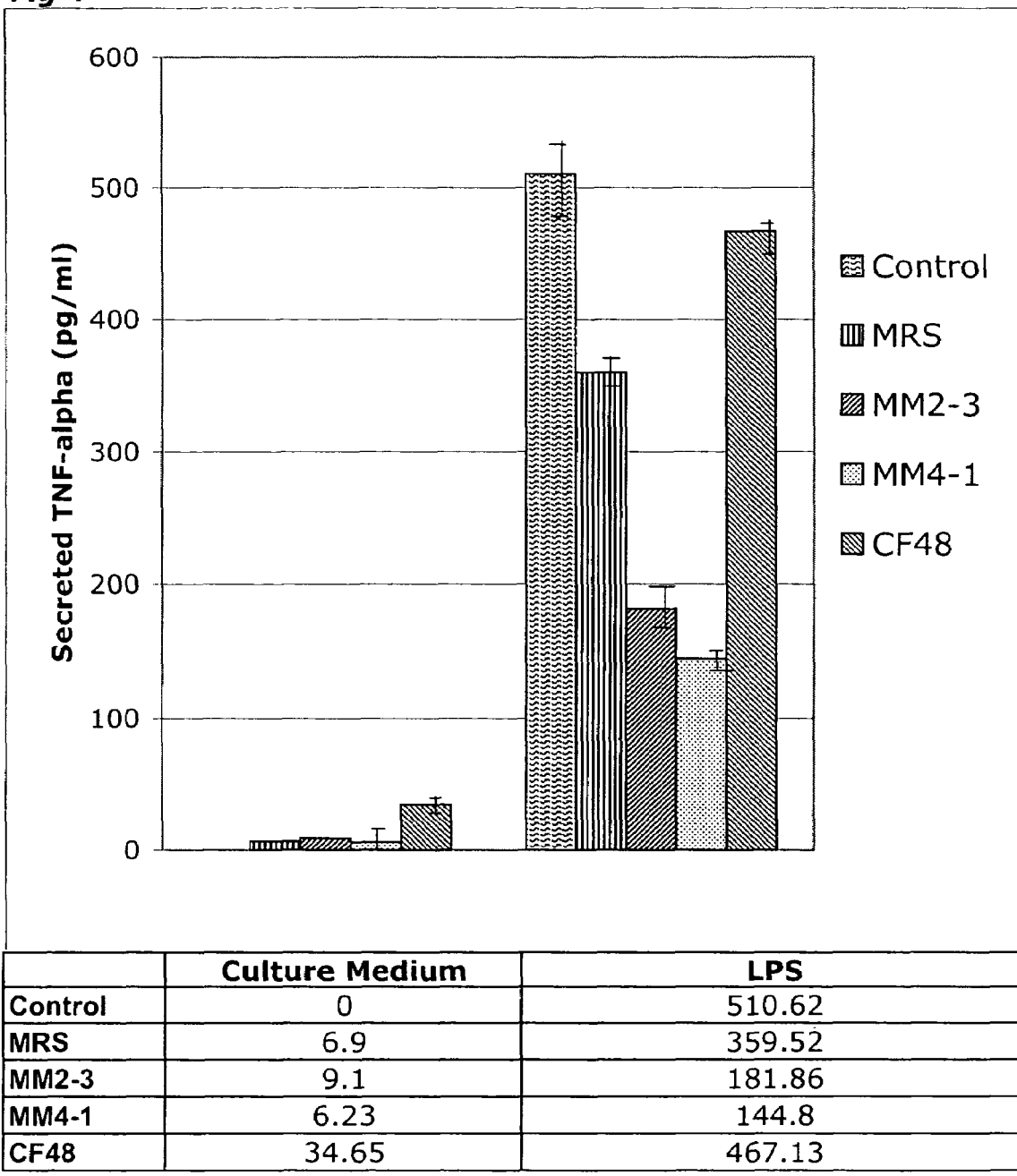

SELECTION AND USE OF LACTIC ACID BACTERIA FOR REDUCING INFLAMMATION IN MAMMALS

BACKGROUND OF THE INVENTION

1. Field of the Invention

This invention relates to use of a method for screening nonpathogenic anti-inflammatory bacterial strains, and products and methods using such strains for treatment and prophylaxis of unwanted inflammation caused by certain bacteria or other inflammation-causing agents.

2. Description of the Related Art

Monocytes leave the bone marrow and travel through the peripheral blood vessels until they reach the mucosa/serosa of the gastro intestinal tract. These putative macrophages are key to the interaction and propagation of the signals necessary to regulate the immune system of the GI.

In the gastrointestinal tract, there is a constant level of immune response in the macrophages of the mucosal epithelium to the bacteria in the intestinal lumen and attached to the intestinal mucosa. In the normal state, this response involves the generation of cytokine signals to restrict and contain an unnecessary inflammatory response. However, when a pathogen or toxin is presented to these cells, they form the first line of defense and react by producing an increasing amount of pro-inflammatory cytokines, which propagate the inflammatory response until the threat is removed. The generation of cytokines relevant to the interactions with commensal (non-threatening) bacteria as well as those involved in the full inflammatory response to pathogens, are subject to intervention by lactic acid bacteria themselves (including surface antigens) or by substances produced by these lactic acid bacteria and it is clear that the commensal flora has extensive interaction with the macrophages of the mucosa to maintain a balanced reaction to the gut flora and thereby maintain optimal health (Rook G A, Adams V, Hunt J, Palmer R, Martinelli R, Brunet LR. *Mycobacteria* and other environmental organisms as immunomodulators for immunoregulatory disorders. Springer Semin Immunopathol 2004; 25:237-255).

It is known that various pathogens can cause inflammation, for example in the gastrointestinal tract. Such inflammation, for example, in the stomach and gastrointestinal tract, is mediated by intercellular signal proteins known as cytokines which are produced by macrophages and dendritic cells in the epithelium in response to an antigenic stimulus such as that produced by a pathogen. Upon contact between the epithelium and the antigen of a pathogen or endotoxins produced by it, such as LPS, antigen presenting cells (including dendritic cells) in the epithelium propagate the signal to naive macrophages which then respond in a so-called Th-1 type response where pro-inflammatory cytokines including TNFα, IL-1, IL-6, IL-12 are produced by the macrophages. These cytokines in turn stimulate natural killer cells, T-cells and other cells to produce interferon γ (IFNγ), which is the key mediator of inflammation. IFNγ leads to an escalation of the inflammatory response and the reactions described above that lead to cytotoxicity. Naive macrophages can also respond to antigens with a Th-2 type response. This response is suppressed by IFNγ. These Th-2 type cells produce anti-inflammatory cytokines such as IL-4, IL-5, IL-9 and IL-10.

IL-10 is known to inhibit the production of IFNγ and thus dampen the immune response. The balance between Th-1 and Th-2 type cells and their respective cytokine production defines the extent of the inflammation response to a given antigen. Th-2 type cells can also stimulate the production of immunoglobulins via the immune system. Anti-inflammatory activity in the gastrointestinal tract, where there is a reduced TNFα level, correlates with enhanced epithelial cells (gut wall lining integrity) and thus to a reduction in the negative effects caused by gastrointestinal pathogens and toxins.

The results of a number of research studies indicate that DNA can exert an anti-inflammatory action on intestinal epithelial cells, or can stimulate the immune system (Madsen et al. and Rachmilewitz et al, respectively, presentations at Digestive Disease Week, May 19-22, 2002, The Moscone Center, San Francisco).

Inflammation is involved in several diseases in mammals both externally on skin, eyes, etc., and internally for example on various mucous membranes; in the mouth, GI tract, vagina etc. but also in muscles, bone-joints and in brain-tissue. In the GI-tract there are several diseases connected to inflammation, for example, gastritis, ulcer and inflammatory bowel disease (IBD). IBD is a chronic disorder that causes an inflamed and swollen digestive tract or intestinal wall. When the digestive tract becomes inflamed or swollen with IBD, sores (ulcers) form and bleed. This in turn can cause abdominal pain, watery diarrhea, blood in the stool, fatigue, reduced appetite, weight loss, or fever. Thus, inflammation in IBD leads to tissue damage such as ulcers and exacerbated disease in a patient.

The two most common forms of IBD are ulcerative colitis (UC) and Crohn's disease (CD). Crohn's Disease is a chronic condition characterised by recurrent inflammatory lesions of the entire gut wall from mucosa to serosa and can affect many sites in the intestine. The disease has been linked to imbalances in the gut microflora and an overexpressed inflammatory reaction to components of the normal gut flora and this reaction is currently treated with poor success using a series of different drugs, one of which is based on anti-TNFα therapy designed to reduce the levels of TNFα in the gastro-intestinal mucosa. Thus, persons with such a disease form an ideal study group and indeed target group for the use of immuno-modulatory, inflammation attenuating *lactobacilli*.

Mice spontaneously develop chronic colitis, which does not occur in germ-free animals. Mouse colitis is similar to human Crohn's disease, a chronic serious inflammatory disease of the gastrointestinal tract. Crohn's disease usually occurs in the intestines, but may occur anywhere in the gastrointestinal tract. These conditions require the presence of enteric bacteria and are both Th1-mediated-IL-12-dependent forms of colitis.

Because of the similarities of the causes and symptoms, mouse models of colitis and other mouse models are often used to study components of the inflammatory response directly, and, as the same mechanisms are assumed to apply in man, are often accepted to be used as models to develop treatments for human gastrointestinal disease. There are, however, some questions about the relevance of the animal derived models for humans, so there is a need to have alternative methods to study the human mechanisms and to confirm results from other models, in more human based systems. The purpose of the invention herein is to provide a method based on human cells to select lactic acid bacteria that display anti-inflammatory characteristics and then to use such selected lactic acid bacteria for prophylaxis and treatment of various inflammatory diseases.

*Lactobacillus reuteri* is one of the naturally occurring inhabitants of the gastrointestinal tract of animals and is routinely found in the intestines of healthy animals and despite the low pH, occasionally also in the human stomach. It is known to have antibacterial activity. See, for example U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as reuterin (β-hydroxy-propionaldehyde). It is also known that certain strains of *lactobacilli* including *L. reuteri* have anti-inflammatory properties as is in U.S. patent application 20040208863 and 20040067573. Other immunomodulating activity has also been associated with various other *lactobacilli*.

Human clinical trials and animal studies have shown that *Lactobacillus* can prevent or improve inflammation in chronic colitis. It is hypothesised that *lactobacilli* are capable of down-regulating pro-inflammatory cytokine responses induced by enteric bacteria. J. Peña et al (2003) investigated whether *lactobacilli* diminish production of tumour necrosis factor alpha (TNF α) by a murine macrophage line. It was shown that TNF-α production by murine macrophages incubated with *Lactobacillus rhamnosus* GG and lipopolysaccharides was significantly inhibited compared to controls.

The same group of workers investigated whether *Lactobacillus* spp. might be effective in ameliorating *Helicobacter*-induced inflammation in vivo. For this, co-inoculation experiments with *L. reuteri* and *L. paracasei* were performed in the *H. hepaticus* mouse colitis model. A significant decrease in pathology scores was observed in female mice that have received both *H. hepaticus* and *Lactobacillus* spp. when compared to animals given *H. hepaticus* alone. The probiotic effect of *Lactobacillus* spp. in this model was shown to be independent of the exclusion of *H. hepaticus* bacteria, but dependent on post-transcriptional regulation of TNF-α expression. The data suggests the existence of a novel mechanism by which *Lactobacillus* spp. can down-regulate *Helicobacter* induced pro-inflammatory cytokine production in macrophages.

Patent WO2004/031368A1 describes *Lactobacillus* strains selected for its ability to reduce gastrointestinal inflammation associated with *H. pylori* infection in mammals using a mouse macrophage assay for TNF-α activity.

Patent application US20040057943A1 relates to a process for selection of new probiotic strain of *L. coryniformis, L. salivarius, L. acidofilus, L. gasseri* and *L. fermentum* that are capable of surviving in breast milk and/or amniotic fluid.

S. Ménard et al. (2003) investigated whether lactic acid bacteria secreted metabolites that retain anti-inflammatory properties after intestinal transport. Analysis of LPS binding to THP-1 pro-monocytes in the presence of bacteria conditioned media (CM) was made to see if LPS has to bind to LPS binding protein (LBP) before LPS-LBP can recognize the CD14 receptor. The binding was measured by flow cytometry. It was shown that *Bifidobacterium* and *Streptococcus thermofilus* CM completely inhibited LDB dependent LPS binding to THP-1 cells by releasing metabolites exerting an anti TNF-α effect capable of crossing the intestinal barrier.

While the differences in the ability of several *lactobacilli* to reduce inflammation, including gastrointestinal inflammation, is known, it was not previously known that these differences are better predicted by using a model based on human cells and that such a model is preferred to select such strains for potential effect in humans.

It is therefore an object of the invention to provide strains of lactic acid bacteria, which have been selected using human cell lines, for their capability of reducing inflammation, such as that due to IBD. It is a further object of the invention to provide products containing said strains, including agents for treatment or prophylaxis of inflammation, for example associated with IBD for administration to humans and other mammals, including conditioned media in which said strains have grown and protein-containing extracts thereof. Thus, the invention is used to treat inflammation in IBD which leads to tissue damage such as ulcers and exacerbated disease in a patient.

Other objects and advantages will be more fully apparent from the following disclosure and appended claims.

SUMMARY OF THE INVENTION

The invention herein provides novel strains of lactic acid bacteria selected for their capability of reducing inflammation, such as intestinal bowel disease, a method of selecting such strains, and products containing such strains.

BRIEF DESCRIPTION OF THE DRAWINGS

FIG. 4 is a bar graph showing the effect of *Lactobacillus*-conditioned media on TNF-α production by LPS-activated primary monocytes. Primary monocytes from CD-act patients were used. The strains and controls were incubated 24 hours.

DETAILED DESCRIPTION OF THE INVENTION AND PREFERRED EMBODIMENTS THEREOF

Figure 1:
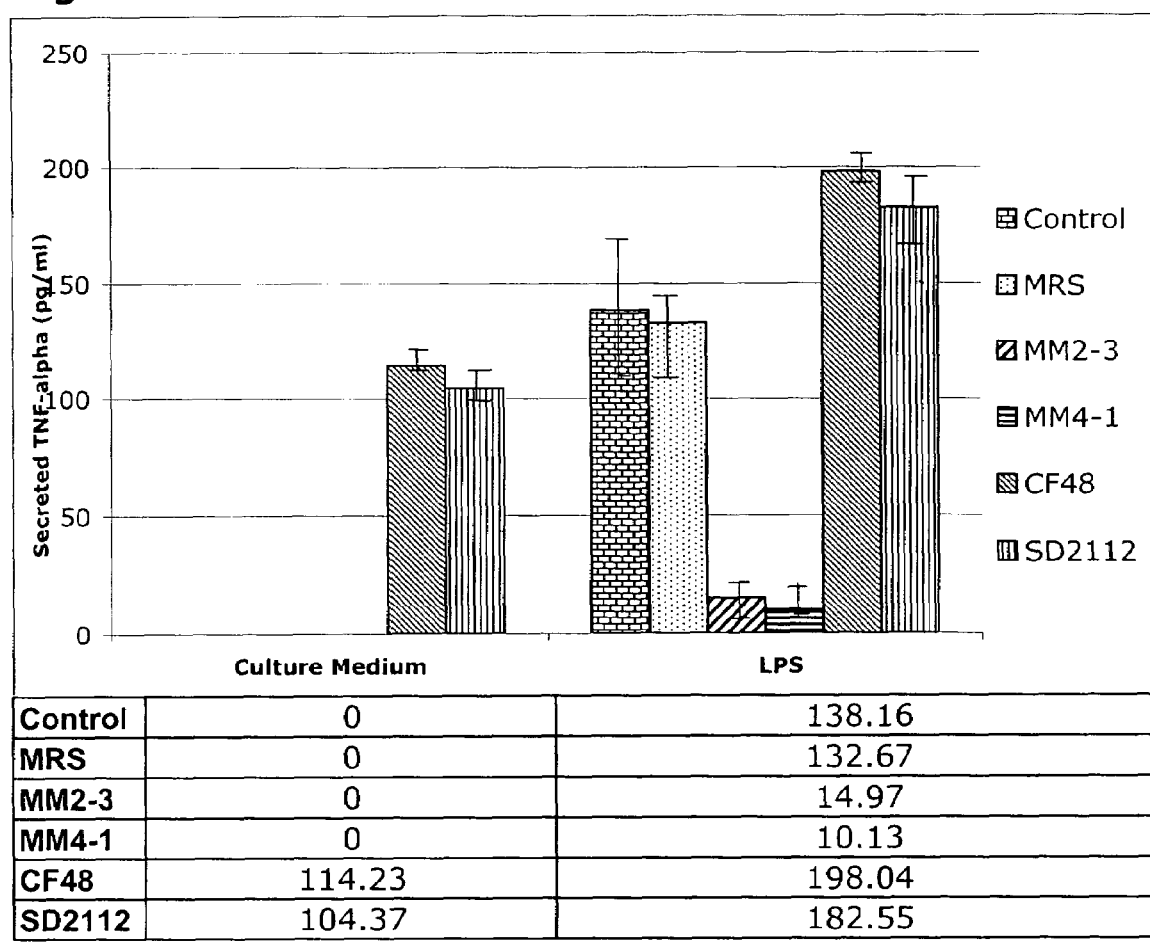
FIG. 1 is a bar graph showing the effect of *Lactobacillus*-conditioned media on TNF-α production by LPS-activated monocytes. Three strains and controls were incubated 24 hours.

The present invention herein comprises strains of lactic acid bacteria which have been selected for their capability of reducing inflammation, such as in IBD. Such strains include *Lactobacillus reuteri* MM4-1A, ATCC PTA-6475. This strain is available to the public at the American Type Culture Collection (10801 Univ. Blvd., Manassas, Va.) having been deposited there under the Budapest Treaty on Dec. 21, 2004. Products such as foods, nutritional additives and formulations, pharmaceuticals or medical devices containing whole cells or components derived from these strains may be formulated as is known in the art, and generally include an ingestible support as known plus the *Lactobacillus*-strain, or its derived component. Previously known strains, now identified to have good TNFα reducing capacity, such as *L. rhamnosus* GG ATCC 53103, *L. reuteri* MM2-3, ATCC PTA-4659 and others, can also be used in above formulations.

Model systems using the appropriate cytokines are used to determine factors that reduce or increase inflammation. In the invention provided herein, an assay based on human cells is used.

THP-1 cells are a human monocytic cell line derived from leukemia patient and which are maintained at the American Type Culture Collection. The origin of these cells from a human host makes them particularly relevant to study interactions of the human gastro-intestinal immune system with human commensal bacteria.

Data in this invention disclose an indication of a powerful inhibition of TNFα production by the specific strains *L. reuteri* ATCC PTA 4659 and *L. reuteri* ATCC PTA 6475 and that this inhibition is mediated by a substance released into the growth medium by these two specific strains during late log/stationary growth phase. On the contrary, two other strains of *L. reuteri*, were not only unable to inhibit the inflammatory response of the cells to *E. coli* toxin, but also induced an inflammatory response themselves. This surprising finding indicates a potential, anti-inflammatory properties of the strains *L. reuteri* ATCC PTA 4659 and *L. reuteri* ATCC PTA 6475 which could not be predicted.

To confirm the possible clinical relevance of these findings further studies were performed in cells derived from the blood of patients with inflammatory bowel disease, specifically Crohn's disease (CD).

To study the interactions between lactic acid bacteria and the mucosal immune cells, we considered differentiated macrophages to be a better model than undifferentiated monocytes. Such differentiated macrophages are more likely to resemble the in vivo macrophage cell population of the gastrointestinal tract responding to the lactic acid bacteria and eliciting the regulatory or inflammatory changes of the innate host immune system. For example, the production of pro-inflammatory interleukin-8 by THP-1 cells in response to endotoxins was markedly increased after induction of differentiation (Baqui et al., 1999) and further, TNFα production by these cells is significantly increased after differentiation (Klegeris et al., 1997).

The features of the present invention will be more clearly understood by reference to the following examples, which are not to be construed as limiting the invention.

Example 1

Selection of Anti-Inflammatory Strains

THP-1 cells were incubated together with either control media or conditioned media (L-CM) from the growth of selected *L. reuteri* strains, *L. reuteri* ATCC PTA 4659, *L. reuteri* ATCC PTA 6475, *L. reuteri* ATCC 55730 and *L. reuteri* strain CF48-3A. The conditioned media (L-CM) are cell-free supernatants from 9-hour or 24-hour cultures of each of the *L. reuteri* cultures. THP-1 cells were stimulated with either control medium or *E. coli*-derived LPS (which leads to the generation of TNFα in a normal inflammatory response) during a 3.5 hour incubation after which the cells were removed and the supernatants assayed for TNFα levels using an ELISA technique.

Materials:

THP-1 leukemic monocytic cell line (ATCC, cat number TIB202)

RPMI 1640 Medium (Gibco-Invitrogen)

Fetal Bovine Serum (Gibco-Invitrogen)

Penicillin-Streptomycin solution (Sigma)

*E. coli* Serotype O127:B8 Lipopolysaccharide (Sigma, cat number L3137)

TNF-alph/TNF-SFII human DuoSet ELISA Development Kit (R&D Systems, cat number DY210)

Method:

Use THP-1 monocytic cell line. Add 5% (v/v) of MRS media and 5% (v/v) of *Lactobacillus* conditioned medium into the appropriate wells. *Lactobacillus* conditioned medium is supernatant from a 24-hour culture of *Lactobacillus* species in MRS media. The conditioned medium is then pH-adjusted by speed-vacuum drying and the pellet resuspended in equal volume of culture medium. Although the humidified chamber is designed to minimize liquid evaporation, after 48 hours of incubation, the cell suspension volume in the 24-well plates is reduced to about 475 μl.

Add 100 ng/ml of *E. coli* serotype O127:B8 lipopolysaccharide into the appropriate wells. Incubate in a 37° C., humidified, 5% $CO_2$ chamber. After 3.5 hours of incubation, collect cultures into 1.5 ml centrifuge tubes. Centrifuge at 1500 RCF for 5 minutes in 4° C. Collect supernatants.

Test for cytokine expression by ELISA (Quantikine TNF-alph/TNF-SFII human DuoSet).

The culture medium used was 10% FBS, 2% Penicillin-Streptomycin in RPMI 1640.

Results—Example 1

Incubation of THP-1 cells with 24-hour L-CM from *L. reuteri* ATCC PTA 4659, *L. reuteri* ATCC PTA 6475 strains in the absence of LPS did not lead to the generation of TNFα in the incubation medium (FIG. 1). Surprisingly, L-CM from *L. reuteri* ATCC 55730 and *L. reuteri* strain CF48-3A stimulated the production of TNFα by the THP-1 cells to levels similar to those seen with LPS alone. Thus, the *L. reuteri* strains differ in their ability to stimulate pro-inflammatory TNFα production by resting THP-1 monocytes.

Addition of LPS to the THP-1 cells in the absence of L-CM led to the generation of 138 pg/ml TNFα during the 3.5 hour incubation period. This is the expected inflammatory response of the THP-1 cells to the toxin. Addition of the growth medium (MRS), which acts as a control for the L-CM additions, led to the generation of 132 pg/ml TNFα and thus MRS did not interfere with the response to LPS. The addition of 24-hour L-CM from *L. reuteri* ATCC PTA 4659 or *L. reuteri* ATCC PTA 6475 dramatically reduced the levels of LPS stimulated TNFα to only 14 and 10 pg/ml, respectively. This represents an inhibition of LPS-stimulated TNFα production of 89 and 92%, respectively. On the contrary, in the presence of 24-hour L-CM from *L. reuteri* ATCC 55730 and *L. reuteri* strain CF48-3A, LPS was still able to induce a significant rise in TNFα compared to the levels in the absence of LPS. LPS-stimulated TNFα production increased by 50% and 38% despite the presence of L-CM from *L. reuteri* ATCC 55730 and *L. reuteri* strain CF48-3A, respectively.

Figure 2:
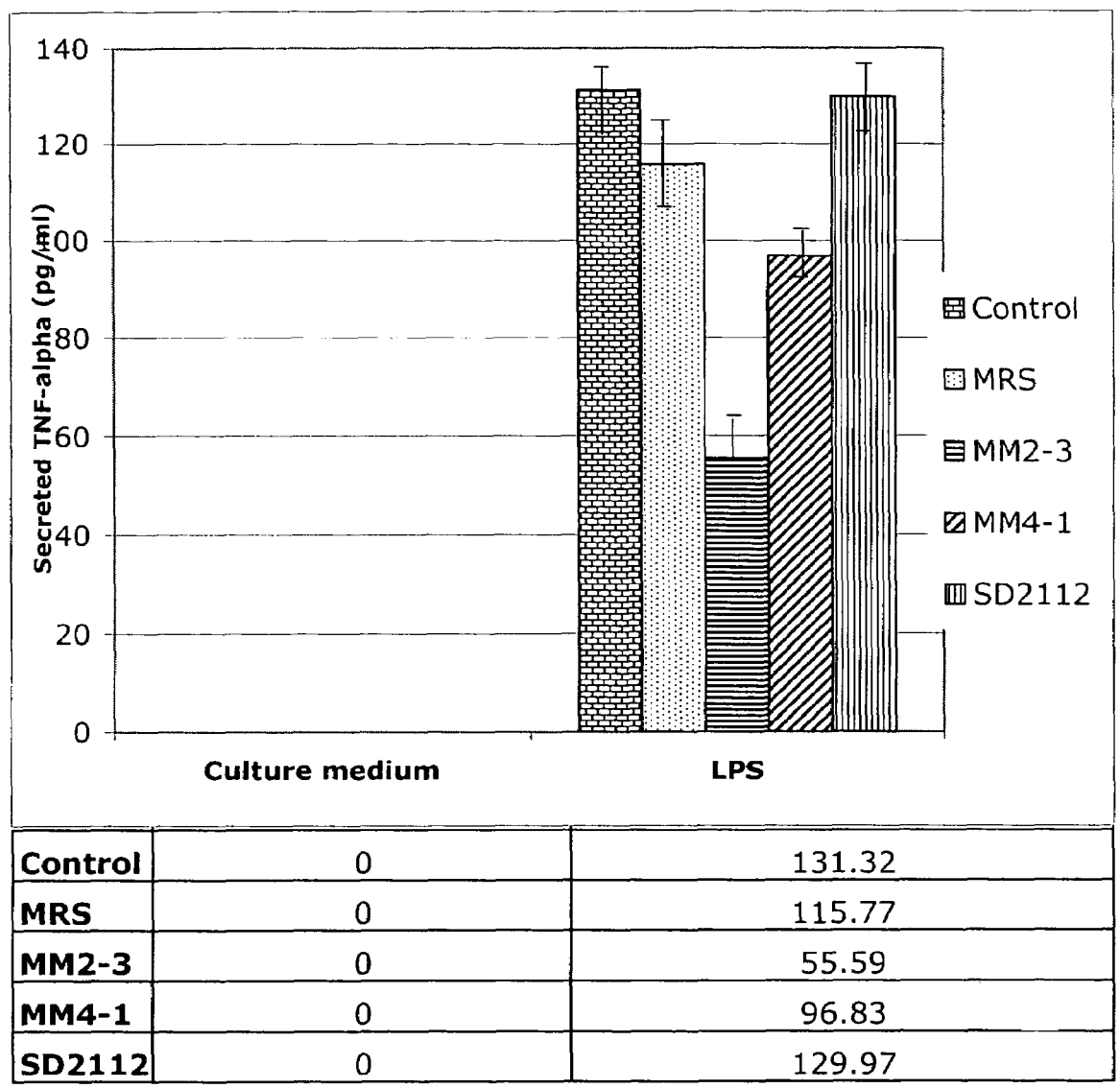
FIG. 2 is a bar graph showing the effect of *Lactobacillus*-conditioned media on TNF-α production by LPS-activated monocytes. Three strains and controls were incubated 9 hours.

Similar experiments performed with 9-hour L-CM from *L. reuteri* ATCC PTA 4659 or *L. reuteri* ATCC PTA 6475 demonstrated that the inhibitory effect on LPS-stimulated TNFα production was considerably less (52% and 16%, respectively; FIG. 2) but still there. Thus, longer incubations of the *L. reuteri* strains, with harvesting of the L-CM in late log/stationary phase of growth, leads to improved efficacy in inhibiting TNFα production.

Example 2

Negative Selection Prep for Monocyte Cells

The Monocyte Isolation Kit II (Miltenyi Biotec, Inc. 12740 Earhart Avenue, Auburn, Calif. 95602 (800) 367-6227; http://www.miltenyibiotec.com/index.php?, order number 130-091-153) is an indirect magnetic labeling system for the isolation of untouched monocytes from human peripheral blood mononuclear cells (PBMC). Non-monocytic cells, i.e., T cells, B cells, NK cells, dendritic cells, and basophils are indirectly magnetically labeled using a cocktail of biotin-conjugated antibiotics against CD3, CD7, CD16, CD19, CD56, CD123 and Glycophorin A, and Anti-Biotin MicroBeads. In between the two labeling steps, no washing steps are required. The magnetically-labeled non-monocytes are depleted by retaining them on a MACS® Column in the magnetic field of a MACS Separator, while the unlabeled monocytes pass through the column. Isolation of relatively enriched unlabeled monocytes is achieved by depletion of the magnetically labeled cells. Level of enrichment may be assessed or confirmed by flow cytometry.

Kit Information: Monocyte Isolation Kit II (Order number 130-091-153). Kit Contents: FcR Blocking Reagent (1 ml); Biotin-Antibody Cocktail (1 ml); Anti-Biotin MicroBeads (2 ml); Materials and Equipment Not Supplied in Kit: 15 ml Corning centrifuge tubes; Refrigerated centrifuge; Pipettes and pipette tips; Serological pipetors and pipet tips; Timer; Miltenyi Biotec MACS® MS column; Miltenyi Biotec MACS® magnet; Miltenyi Biotec MACS® column stand; Hausser Scientific Bright-Line hemocytometer; Working buffer (WB): sterile 1× phosphate buffered saline (PBS, pH 7.4, Gibco catalog number 10010023)+0.5% bovine serum albumin (BSA, Panvera catalog number P2489)+2 mM ethylenediaminetetraacetic acid (EDTA, Gibco catalog number 15553-035)

Method (Monocyte Isolation Kit II):

Determine the cell density by counting on a hemocytometer. Transfer cell suspension into a 15 ml Corning conical tube. Pellet cells at 300 RCF for 10 minutes in 4° C. Remove supernatant using a 10 ml serological pipet. Resuspend cell pellet in 30 µl of WB per $10^7$ total cells. Add 10 µl of FcR Blocking Reagent per $10^7$ total cells. Add 10 µl of Biotin-Antibody Cocktail per $10^7$ total cells. Mix well and incubate for 10 minutes at 4°-8° C. Add 30 µl of WB per $10^7$ total cells. Add 20 µl of Anti-Biotin MicroBeads per $10^7$ total cells. Mix well and incubate for an additional 15 minutes at 4°-8° C. Wash cells by adding 10-20× labeling volume of WB. Centrifuge at 300 RCF for 10 minutes in 4° C. Remove supernatant using a 2 ml serological pipet. Resuspend cell pellet in 500 µl of WB per $10^8$ cells. Place MACS MS column on the magnet.

Wash column with 500 µl of WB. Load cell suspension onto the column. Let drain through and into a collection tube (4 min/ml). Wash column with 3×500 µl of WB and let drain through into the same collection tube.

Elute captured cells into another collection tube by placing column into another tube, pipette 1 ml of WB into column and flush out cells using positive pressure with plunger supplied with the column. Push through at a rate of 2 seconds/inch.

In the above protocol it is important to work fast and use cold solutions only. Working on ice requires increased incubation times for MACS MicroBeads. Incubate in refrigerator at 4°-8° C. Buffers or media should not contain $Ca^{2+}$ or $Mg^+$. BSA may be replaced by other proteins such as gelatin, human serum albumin or fetal calf serum. The type of anti-coagulant used does not affect protocol. Higher temperatures and longer incubation times may lead to non-specific cell labeling.

Example 3

Primary Monocyte Bioassay

Primary human monocytes were isolated from the blood of CD patients who were in a phase of active inflammation (CD-act) or were in remission (CD-rem) where the inflammation had subsided. Blood was drawn from the CD patients and peripheral blood mononuclear cells isolated. Peripheral blood monocytes were enriched using method in example 2. Suspensions of these were allowed to differentiate for 48 hours in a 37° C., humidified, 5% $CO_2$ chamber. After this procedure, the cells have developed into macrophages. Growth media (control) or L-CM were then added to either peripheral blood monocytes or the differentiated macrophages and the cells were stimulated with either control medium or E. coli-derived LPS and incubated for 3.5 hours. TNFα production in the supernatants from these incubations was analyzed.

The materials used were: Primary peripheral blood monocytes; RPMI 1640 Medium (Gibco-Invitrogen); Fetal Bovine Serum (Gibco-Invitrogen); Penicillin-Streptomycin solution (Sigma); E. coli Serotype O127:B8 Lipopolysaccharide (Sigma, cat number L3137); trans Retinoic Acid (CalBioChem, cat number 554720); TNF-alph/TNF-SFII human DuoSet ELISA Development Kit (R&D Systems, cat number DY210).

The peripheral blood monocytes are isolated as described in the protocols: Peripheral blood mononuclear cells Isolation Protocol (described in example 2) and Monocyte Negative Selection Protocol (described in example 2). Change the cell suspension media (PBS) to cell culture media (10% FBS, 2% Penicillin-Streptomycin in RPMI 1640).

Dilute cells to $1.0 \times 10^5$ cells/ml. Plate 500 µl cell suspension into each well of a 24-well microtiter plate. Allow cells to differentiate for 48 hours in a 37° C., humidified, 5% $CO_2$ chamber. Start bioassay. Add 5% (v/v) of MRS media and 5% (v/v) of Lactobacillus conditioned media into the appropriately wells. Lactobacillus conditioned media is supernatant from a 24-hour culture of Lactobacillus species in MRS media. The conditioned media is then pH-adjusted by speed-vacuum drying and the pellet resuspended in equal volume of culture media. Although the humidified chamber is designed to minimize liquid evaporation, after 48 hours of incubation, the cell suspension volume in the 24-well plates is reduced to about 475-485 µl. Add 100 ng/ml of E. coli serotype O127:B8 lipopolysaccharaide into the appropriate wells. Incubate in a 37° C., humidified, 5% $CO_2$ chamber. After 3.5 hours of incubation, collect cultures into 1.5 ml centrifuge tubes. Centrifuge at 1500 RCF for 5 minutes in 4° C. Collect supernatants. Test for cytokine expression by ELISA (Quantikine TNF-alph/TNF-SFII human DuoSet).

Results—Example 3

Figure 3:
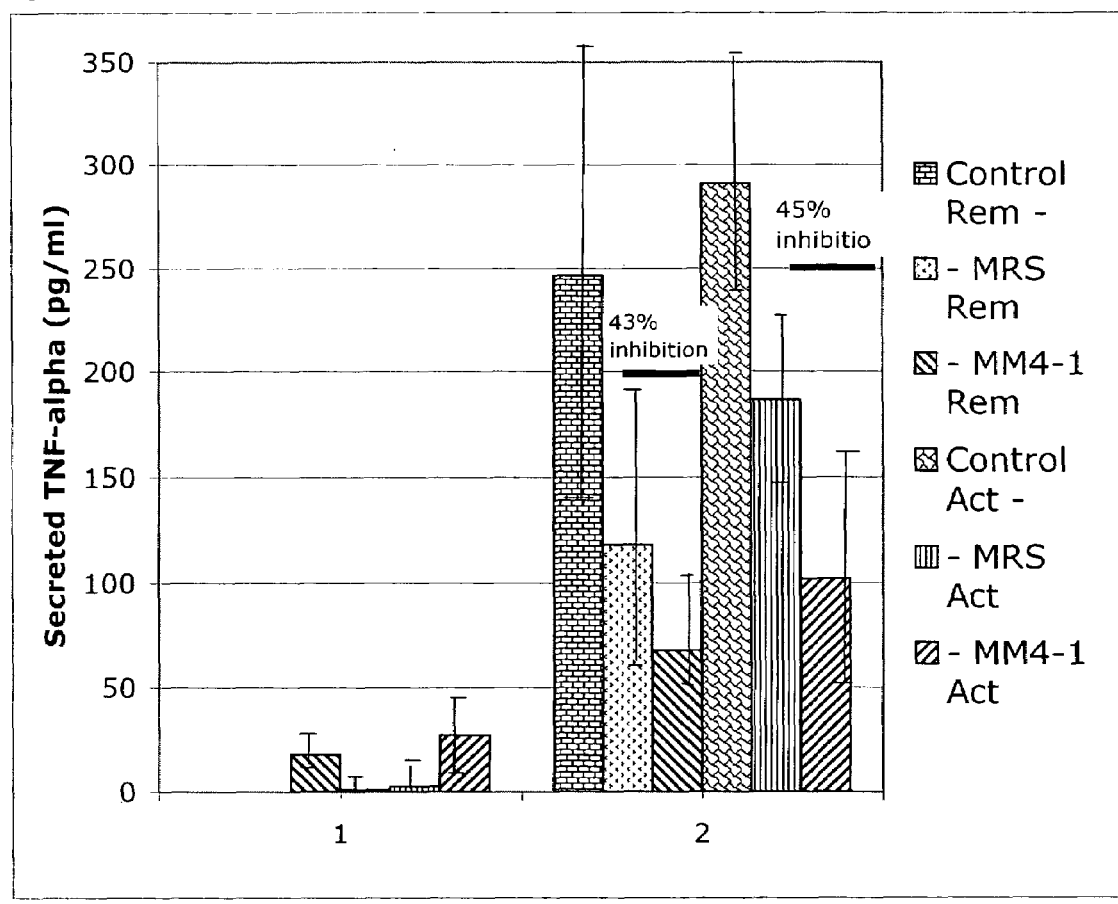
FIG. 3 is a bar graph showing the inhibition of *Lactobacillus*-conditioned media on TNF-α production by LPS-activated primary monocytes. Primary monocytes from CD-rem (remission) and CD-act (active) patients were used. The strains and controls were incubated 24 hours.

In primary monocytes from CD-rem patients, LPS led to the expected elevation in TNFα and this elevation could be inhibited by 43% in the presence of L-CM from L. reuteri ATCC PTA 6475. In primary monocytes from CD-act patients, the level of LPS-stimulated TNFα production was somewhat higher and was inhibited to the same degree by L-CM from L. reuteri ATCC PTA 6475 (FIG. 3).

Compared to medium controls, the production of TNFα in response to LPS in differentiated macrophages derived from primary monocytes from CD-act patients, was significantly inhibited by 50% by L-CM from L. reuteri ATCC PTA 4659 and by 60% by L-CM from L. reuteri ATCC PTA 6475 (FIG. 4). Confirming the data from the THP-1 cells, L-CM derived from L. reuteri ATCC 55730 and L. reuteri strain CF48-3A were unable to inhibit the production of TNFα and on the contrary, increased the production of TNFα by 22% and 30%, respectively compared to the relevant controls (FIG. 4).

These data confirm the surprising finding that the different strains of L. reuteri have varying effects on TNFα production by monocytes and differentiated macrophages and that strains *L. reuteri* ATCC PTA 4659 and *L. reuteri* ATCC PTA 6475 are particularly suitable for use in the gastro-intestinal tract of humans with inflammatory bowel disease.

Example 4

Use of the Conditioned Medium

Using the method in example 1, the conditioned medium from one effectively TNFα decreasing strain was selected, in this experiment the medium from *L. reuteri* ATCC PTA-4659. This medium was produced in larger scale by growing the strain in de Man, Rogosa, Sharpe (MRS) (Difco, Sparks, Md.). Overnight cultures of *lactobacilli* were diluted to an $OD_{600}$ of 1.0 (representing approximately $10^9$ cells/ml) and further diluted 1:10 and grown for an additional 24 h. Bacterial cell-free conditioned medium was collected by centrifugation at 8500 rpm for 10 min at 4° C. Conditioned medium was separated from the cell pellet and then filtered through a 0.22 μm pore filter unit (Millipore, Bedford, Mass.). The conditioned medium was then lyophilized and formulated, using standard methods, to make a tablet. This tablet was used as a drug by humans to effectively treat ulcer caused by IBD.

Example 5

Use of Selected Anti-Inflammatory *Lactobacillus reuter* Strains

Using the method in example 1, the conditioned medium from one effectively TNFα decreasing strain was selected, in this experiment the medium from *L. reuteri* ATCC PTA-4659. The *L. reuteri* strain was then lyophilized and formulated, using standard methods, to make a capsule. This capsule was used as a drug by humans to effectively effectively reduce inflammation of the mucosa in IBD patients caused by IBD.

Example 6

Characterization of Protein Produced by Effective *Lactobacillus* Strains

Different effective *Lactobacillus* conditioned media, including the *L. reuteri* strain ATCC PTA 4659, and *L. reuteri* ATCC PTA-6475 conditioned medium, were treated with various denaturing compounds to determine the nature of the putative immunomodulins derived from the bacteria. Thus, conditioned media were subjected to repetitive freeze-thawing, heat treatment, digestion with DNA digesting enzymes, proteases and inactivated proteases. The putative immunomodulin was in this way determined to be one or more proteins or peptides in nature. To determine the size of the putative protein immunomodulin, the conditioned medium was fractionated by filtration and the filtrates tested for effectiveness. In this way, the active component of the conditioned media of effective *Lactobacillus* strains was found to be approx 5 kDa in size or less.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A biologically pure culture of *Lactobacillus reuteri* ATCC PTA-6475.

2. A method for treating inflammation in inflammatory bowel disease, comprising orally administering gastronintestinally to a human conditioned medium from a culture according to claim 1.

* * * * *